US006799066B2

(12) United States Patent
Steines et al.

(10) Patent No.: US 6,799,066 B2
(45) Date of Patent: Sep. 28, 2004

(54) TECHNIQUE FOR MANIPULATING MEDICAL IMAGES

(75) Inventors: Daniel Steines, Palo Alto, CA (US); Philipp Lang, Lexington, MA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 52 days.

(21) Appl. No.: 09/953,531

(22) Filed: Sep. 14, 2001

(65) Prior Publication Data

US 2002/0147392 A1 Oct. 10, 2002

Related U.S. Application Data

(60) Provisional application No. 60/232,637, filed on Sep. 14, 2000, and provisional application No. 60/232,639, filed on Sep. 14, 2000.

(51) Int. Cl.[7] .................................................. A61B 5/00
(52) U.S. Cl. ....................... 600/407; 382/128; 382/199
(58) Field of Search ................................. 600/407, 410; 382/128, 190, 199

(56) References Cited

U.S. PATENT DOCUMENTS

| 4,655,227 | A | 4/1987 | Gracovetsky |
| 4,699,156 | A | 10/1987 | Gracovetsky |
| 4,813,436 | A | 3/1989 | Au |
| 4,823,807 | A | 4/1989 | Russell et al. |
| 5,099,859 | A | 3/1992 | Bell |
| 5,154,178 | A | 10/1992 | Shah |
| 5,246,013 | A | 9/1993 | Frank et al. |
| 5,320,102 | A | 6/1994 | Paul et al. |
| 5,413,116 | A | 5/1995 | Radke et al. |
| 5,433,215 | A | 7/1995 | Athanasiou et al. |
| 5,445,152 | A | 8/1995 | Bell et al. |
| 5,503,162 | A | 4/1996 | Athanasiou et al. |

(List continued on next page.)

FOREIGN PATENT DOCUMENTS

WO    WO 02/22014    3/2002

OTHER PUBLICATIONS

Van der Linden et al. "MR imaging of hyaline cartilage of 0.5 T: a quantitative and qualitative in vitro evaluation of three types of sequences." *Skeletal Radiol* 1998, 27: 297–305.

Herberhold C, et al. "An MR–Based Technique for Quantifying the Deformation of Articular Cartilage During Mechanical Loading in an Intact Cadaver Joint." *Magnetic Resonance in Medicine* 1998, 39(5): 843–850.

(List continued on next page.)

*Primary Examiner*—Ruth S. Smith
(74) *Attorney, Agent, or Firm*—Robins & Pasternak LLP

(57) ABSTRACT

The invention and the embodiments described in this invention provide new techniques for manipulating digital images and is particularly useful for extracting tissues (i.e., assigning tissue boundary locations) from medical images. These techniques can be applied to diagnosing arthritis and for monitoring disease progression or response to therapeutic intervention. The invention provides for means to extract the articular cartilage from medical images for analysis purposes.

15 Claims, 4 Drawing Sheets

A.

B.

U.S. PATENT DOCUMENTS

| | | |
|---|---|---|
| 5,541,515 A | 7/1996 | Tsujita |
| 5,564,437 A | 10/1996 | Bainville et al. |
| 5,682,886 A | 11/1997 | Delp et al. |
| 5,749,362 A | 5/1998 | Funda et al. |
| 5,772,595 A | 6/1998 | Votruba et al. |
| 5,779,651 A | 7/1998 | Buschmann et al. |
| 5,810,006 A | 9/1998 | Votruba et al. |
| 5,824,085 A | 10/1998 | Sahay et al. |
| 5,853,746 A | 12/1998 | Hunziker |
| 5,880,976 A | 3/1999 | DiGioia III et al. |
| 5,899,859 A | 5/1999 | Votruba et al. |
| 5,913,821 A | 6/1999 | Farese et al. |
| 5,928,945 A | 7/1999 | Seliktar et al. |
| 5,995,738 A | 11/1999 | DiGioia, III et al. |
| 6,002,859 A | 12/1999 | DiGioia, III et al. |
| 6,078,680 A * | 6/2000 | Yoshida et al. ............. 382/128 |
| 6,161,080 A | 12/2000 | Aouni-Ateshian et al. |
| 6,175,655 B1 | 1/2001 | George, III et al. |
| 6,205,411 B1 | 3/2001 | DiGioia, III et al. |
| 6,249,692 B1 | 6/2001 | Cowin |
| 6,289,753 B1 | 9/2001 | Basser et al. |
| 6,310,477 B1 | 10/2001 | Schneider |
| 6,310,619 B1 | 10/2001 | Rice |
| 6,316,153 B1 | 11/2001 | Goodman et al. |
| 6,334,066 B1 | 12/2001 | Rupprecht et al. |
| 6,450,978 B1 | 9/2002 | Brosseau et al. |
| 6,533,737 B1 | 3/2003 | Brosseau et al. |
| 6,560,476 B1 | 5/2003 | Pelletier et al. |
| 2002/0016543 A1 | 2/2002 | Tyler |
| 2002/0087274 A1 | 7/2002 | Alexander et al. |
| 2002/0147392 A1 | 10/2002 | Steines et al. |
| 2003/0015208 A1 | 1/2003 | Lang et al. |

OTHER PUBLICATIONS

Adam G, et al. "MR Imaging of the Knee: Three-Dimensional Volume Imaging Combined with Fast Processing." *J Comput Asst Tomogr* 1989 Nov.–Dec.; 13(6): 984–988.

Adams ME, et al. "Quantitative Imaging of Osteoarthritis." *Semin Arthritis Rheum* 1991 Jun.; 20(6) Suppl. 2: 26–39.

Ahmad CS, et al. "Biomechanical and Topographic Considerations for Autologous Osteochondral Grafting in the Knee." *Am J Sports Med* 2001 Mar.–Apr.; 29(2): 201–206.

Aro HT, et al. "Clinical Use of Bone Allografts." *Ann Med* 1993; 25: 403–412.

Beckmann N, et al. "Noninvasive 3D MR Microscopy as a Tool in Pharmacological Research: Application to a Model of Rheumatoid Arthritis." *Magn Reson Imaging* 1995; 13(7): 1013–1017.

Burgkart R, et al. "Magnetic Resonance Imaging–Based Assessment of Cartilage Loss in Severe Osteoarthritis." *Arth Rheum* 2001 Sep.; 44(9): 2072–2077.

Castriota–Scanderbeg A, et al. "Precision of Sonographic Measurement of Articular Cartilage: Inter– and Intraobserver Analysis." *Skeletal Radiol* 1996; 25: 545–549.

Clarke IC, et al. "Human Hip Joint Geometry and Hemiarthroplasty Selection." *The Hip.* C.V. Mosby, St. Louis: 1975. pp 63–89.

Creamer P, et al. "Quantitative Magnetic Resonance Imaging of the Knee: A Method of Measuring Response to Intra–Articular Treatments." *Ann Rheum Dis* 1997; 56: 378–381.

Dupuy DE, et al. "Quantification of Articular Cartilage in the Knee with Three–Dimensional MR Imaging." *Acad Radiol* 1996; 3: 919–924.

Eckstein F, et al. "Accuracy of Cartilage Volume and Thickness Measurements with Magnetic Resonance Imaging." *Clin Orthop* 1998; 352: 137–148.

Eckstein F, et al. "Magnetic Resonance Chondro–Crassometry (MR CCM): A Method for Accurate Determination of Articular Cartilage Thickness?" *Magn Reson Med* 1996; 35: 89–96.

Eckstein F, et al. "The Influence of Geometry on the Stress Distribution on Joints—A Finite Element Analysis." *Anat Embryol* 1994; 189: 545–552.

Eckstein F, et al. "The Morphology of Articular Cartilage Assessed by Magnetic Resonance Imaging: Reproducibility and Anatomical Correlation." *Surg Radiol Anat* 1994; 16: 429–438.

Gersovich EO. "A Radiologist's Guide to the Imaging in the Diagnosis and Treatment of Developmental Dysplasia of the Hip." *Skeletal Radiol* 1997; 26: 447–456.

Haubner M, et al. "A Non–Invasive Technique for 3–Dimensional Assessment of Articular Cartilage Thickness Based on MRI Part 2: Validation Using CT Arthography." *Magn Reson Imaging* 1997; 15(7): 805–813.

Herrmann JM, et al. "High Resolution Imaging of Normal and Osteoarthritic Cartilage with Optical Coherence Tomography." *J. Rheumatol* 1999; 26: 627–635.

Hughes SW, et al. "Technical Note: A Technique for Measuring the Surface Area of Articular Cartilage in Acetabular Fractures." *Br J Radiol* 1994; 67: 584–588.

Husmann O, et al. "Three–Dimensional Morphology of the Proximal Femur." *J Arthroplasty* 1997 Jun.; 12(4): 444–450.

Ihara H. "Double–Contrast CT Arthrography of the Cartilage of the Patellofemoral Joint." *Clin Orthop* 1985 Sep.; 198: 50–55.

Iida H, et al. "Socket Location in Total Hip Replacement: Preoperative Computed Tomography and Computer Simulation." *Acta Orthop Scand* 1988; 59(1):1–5.

Jonsson K, et al. "Precision of Hyaline Cartilage Thickness Measurements." *Acta Radiol* 1992; 33(3): 234–239.

Kaneuji A, et al. "Three–Dimensional Morphological Analysis of the Proximal Femoral Canal, Using Computer–Aided Design System, in Japanese Patients with Osteoarthrosis of the Hip." *J Orthop Sci* 2000; 5(4): 361–368.

Karvonen RL, et al. "Articular Cartilage Defects of the Knee: Correlation Between Magnetic Resonance Imaging and Gross Pathology." *Ann Rheum Dis* 1990; 49: 672–675.

Koh HL, et al. "Visualization by Magnetic Resonance Imaging of Focal Cartilage Lesions in the Excised Mini–Pig Knee." *J Orthop Res* 1996 Jul.; 14(4): 554–561.

Korkala O, et al. "Autogenous Osteoperiosteal Grafts in the Reconstruction of Full–Thickness Joint Surface Defects." *Int Orthop* 1991; 15(3): 233–237.

Kwak SD, et al. "Anatomy of Human Patellofemoral Joint Articular Cartilage: Surface Curvature Analysis." *J Orthop Res* 1997; 15: 468–472.

Lefebvre F, et al. "Automatic Three–Dimensional Reconstruction and Characterization of Articular Cartilage from High–Resolution Ultrasound Acquisitions." *Ultrasound Med Biol* Nov. 1998; 24(9): 1369–1381.

Lin CJ, et al. "Three–Dimensional Characteristics of Cartilagenous and Bony Components of Dysplastic Hips in Children: Three–Dimensional Computed Tomography Quantitative Analysis." *J Pediatr Orthop* 1997; 17: 152–157.

Marshall KW, et al. "Quantitation of Articular Cartilage Using Magnetic Resonance Imaging and Three–Dimensional Reconstruction." *J Orthop Res* 1995; 13: 814–823.

Mattila KT, et al. "Massive Osteoarticular Knee Allografts: Structural Changes Evaluated with CT." *Radiology* 1995; 196: 657–660.

Milz S, et al. "The Thickness of the Subchondral Plate and Its Correlation with the Thickness of the Uncalcified Articular Cartilage in the Human Patella." *Anat Embryol* 1995; 192: 437–444.

Minas T. "Chondrocyte Implantation in the Repair of Chondral Lesions of the Knee: Economics and Quality of Life." *Am J Orthop* Nov. 1998; 27: 739–744.

Moussa M. "Rotational Malalignment and Femoral Torsion in Osteoarthritic Knees with Patellofemoral Joint Involvement: A CT Scan Study." *Clin Orthop* Jul. 1994; 304: 176–183.

Myers SL, et al. "Experimental Assessment by High Frequency Ultrasound of Articular Cartilage Thickness and Osteoarthritic Changes." *J Rheumatol* 1995; 22: 109–116.

Peterfy CG, et al. "Emerging Applications of Magnetic Resonance Imaging in the Evaluation of Articular Cartilage." *Radiol Clin North Am* Mar. 1996; 34(2): 195–213.

Ruchfeldt PD, et al. "Improved Techniques for Measuring In Vitro the Geometry and Pressure Distribution in the Human Acetabulum—I. Ultrasonic Measurement of Acetabular Surfaces, Sphericity and Cartilage Thickness." *J Biomech* 1981; 14(4): 253–260.

Saied A, et al. "Assessment of Articular Cartilage and Subchondral Bone: Subtle and Progressive Changes in Experimental Osteoarthritis Using 50 MHz Echography In Vitro." *J Bone Miner Res* 1997; 12(9): 1378–1386.

Sittek H, et al. "Assessment of Normal Patellar Cartilage Volume and Thickness Using MRI: an Analysis of Currently Available Pulse Sequences." *Skeletal Radiol* 1996; 25: 55–62.

Soslowsky LJ, et al. "Articular Geometry of the Glenohumeral Joint." *Clin Orthop* 1992 Dec.; 285: 181–190.

Tyler JA, et al. "Detection and Monitoring of Progressive Degeneration of Osteoarthritic Cartilage by MRI." *Acta Orthop Scand* 1995; 66 Suppl. 266: 130–138.

Van Leersum MD, et al. "Thickness of Patellofemoral Articular Cartilage as Measured on MR Imaging: Sequence Comparison of accuracy, reproducibility, and interobserver variation." *Skeletal Radiol* 1995; 24: 431–435.

Waterton JC, et al. "Magnetic Resonance Methods for Measurement of Disease Progression in Rheumatoid Arthritis." *Magn Reson Imaging* 1993; 11: 1033–1038.

Watson PJ, et al. "MR Protocols for Imaging the Guinea Pig Knee." *Magn Reson Imaging* 1997; 15(8): 957–970.

Wayne JS, et al. "Finite Element Analyses of Repaired Articular Surfaces." *Proc Instn Mech Eng* 1991; 205(3): 155–162.

Adam et al., "NMR tomography of the cartilage structures of the knee joint 3D–volume imag combined with a rapid optical–imaging computer," *ROFO Fortschr. Geb. Rontgenstr. Nuklearmed.* 150(1):44–48, 1989.

Bashir et al., "Validation of Gadolinium–Enhanced MRI of GAG Measurement in Human Cartilage".

Borthakur et al., "In Vivo Triple Quantum Filtered Sodium MRI of Human Articular Cartilage".

Bret et al., "Quantitative analysis of biomedical images," University of Manchester, Zeneca Pharmaceuticals, IBM UK, http://www.wiau.man.ac.uk/~ads/imv.

Butterworth et al., Depts of Biomedical Engineering, Medicine, Neurology, & Center for Nuclear Imaging Research, University of Alabama at Birmingham, USA.

Carano et al., "Estimation of erosive changes in rheumatoid arthritis by temporal multispectral analysis".

Chan et al., "Osteoarthritis of the knee: comparison of radiography, CT, and MR imaging to asse extent and severity," *AJR Am J Roentgenol* 157(4):799–806, 1991.

Cohen et al., "Knee cartilage topography, thickness, and contact areas from MRI: in–vitro calibration and in–vivo measurements," *Osteoarthritis and Cartilage* 7:95–109, 1999.

Dardzinski et al., "T1–T2 Comparison in Adult Articular cartilage," *ISMRM Seventh Scientific Meeting*, Philadelphia, PA, May 22–28, 1999.

Dardzinski et al., "Entropy Mapping of Articular Cartilage".

Dufour et al., "A Technique for the Dynamical Evaluation of the Acromiohumeral Distance of the Shoulder in the Seated Position under Open–field MRI".

Eckstein et al., "Side differences of knee joint cartilage volume, thickness, and surface area, and correlation with lower limb dominance—an MRI–based study," *Osteoarthritis and Cartilage* 10: 914–921 (2002).

Eckstein et al., "Determination of knee joint cartilage thickness using three–dimensional magnetic resonance chondro-–crassometry (3D MR–CCM)," *Magn. Reson. Med.* 36(2):256–265, 1996.

Eckstein et al., "New quantitative approaches with 3–D MRI: cartilage morphology, function and degeneration," *Medical Imaging International*, Nov.–Dec., 1998.

Eckstein et al., "Effect of gradient and section orientation on quantitative analyses of knee joint cartilage," *Journal of Magnetic Resonance Imaging* 11: 161–167 (2000).

Eckstein et al., "Functional analysis of articular cartilage deformation, recovery, and fluid flow following dynamic exercise in vivo," *Anatomy and Embryology* 200: 419–424 (1999).

Eckstein et al., "Effect of physical exercise on cartilage volume and thickness in vivo: an MR imaging study," *Radiology* 207: 243–248 (1998).

Faber et al., "Quantitative Changes of Articular Cartilage Microstructure During Compression of an Intact Joint".

Faber et al., "Gender differences in knee joint cartilage thickness, volume and articular surface areas: assessment with quantitative three–dimensional MR imaging," *Skeletal radiology* 30(3):144–150, 2001.

Ghosh et al., "Watershed Segmentation of High Resolution Articular Cartilage Images for assessment of OsteoArthritis".

Glaser et al., "Optimization and validation of a rapid high–resolution T1–w 3D Flash waterexcitation MR sequence for the quantitative assess–ment of articular cartilage volume and thickness," *Magnetic Resonance Imaging* 19: 177–185 (2001).

Goodwin et al., "MR Imaging of Articular Cartilage: Striations in the Radial Layer Reflect the Fibrous Structure of Cartilage".

Graichen et al., "Three–dimensional analysis of the width of the subacromial space in healthy subjects and patients with impingement syndrome," *American Journal of Roentgenology* 172: 1081–1086 (1999).

Gandy et al., "One–year longitudinal study of femoral cartilage lesions in knee arthritis", 1999.

Hall et al., "Quantitation MRI for clinical drug trials of joint disease; Virtual Biopsy of articular cartilage".

Hardy et al., "The influence of the resolution and contrast on measuring the articular cartilage volume in magnetic resonance images," *Magn Reson Imaging.* Oct. 2000; 18(8):965–72.

Hardy et al., "Measuring the thickness of articular cartilage from MR images," *J. Magnetic Resonance Imaging* 13:120–126, 2001.

Hargreaves et al., "MR Imaging of Articular Cartilage Using Driven Equilibrium," *Magnetic Resonance in Medicine* 42(4):695–703 (Oct. 1999).

Hargreaves et al., "MR Imaging of Articular Cartilage Using Driven Equilibrium".

Haut et al., "A High Accuracy Three–Dimensional Coordinate Digitizing System for Reconstructing the Geometry of Diarthrodial Joints," *J. Biomechanics* 31:571–577, 1998.

Herberhold et al., "In situ measurement of articular cartilage deformation in intact femoropatellar joints under static loading," *Journal of Biomechanics* 32: 1287–1295 (1999).

Herberhold et al., "An MR–based technique for quatifying the deformation of articular cartilage during mechanical loading in an intact cadaver joint," *Magnetic Resonance in Medicine* 39: 843–850 (1998).

High et al., "Early Macromolecular Collagen Changes in Articular Cartilage of Osteoarthritis (OA): An In Vivo MT–MRI and Histopathologic Study".

Hohe et al., "Surface size, curvature analysis, and assessment of knee joint incongruity with MR imaging in vivo," *Magnetic Resonance in Medicine*, 47:554–561(2002).

Kaufman et al., "Articular Cartilage Sodium content as a function of compression".

Klosterman et al., "$T_2$ Measurements in Adult Patellar Cartilage at 1.5 and 3.0 Tesla," *ISMRM Seventh Scientific Meeting*, Philadelphia, PA, May 22–28, 1999.

Knauss et al., "Self–Diffusion of Water in Cartilage and Cartilage Components as Studies by Pulsed Field Gradient NMR," *Magnetic Resonance in Medicine* 41:285–292 (1999).

Korhonen et al., "Importance of the superficial tissue layer for the indentation stiffness of articular cartilage," Med Eng Phys. Mar. 2002;24(2):99–108.

Kshirsagar et al., "Measurement of localized cartilage volume and thickness of human knee joints by computer analysis of three–dimensional magnetic resonance images," *Invest Radiol.* May;33(5):289–99, 1998.

Lüsse et al., "Measurement of distribution of water content of human articular cartilage based on transverse relaxation times: an in vitro study".

Merkle et al., "A transceive coil assembly for hetero–nuclear investigations of human breast at 4 T".

Mills et al, "Magnetic resonance imaging of the knee: evaluation of meniscal disease," *Curr. Opin. Radiol.* 4(6):77–82, 1992.

Modest et al., "Optical verification of a technique for in situ ultrasonic measurement of articular cartilage thickness," *J. Biomechanics* 22(2):171–176, 1989.

Mundinger et al., "Magnetic resonance tomography in the diagnosis of peripheral joints," *Schweiz Med. Wochenschr.* 121(15):517–527, 1991, abstract.

Nieminen et al., "$T_2$ Indicates Imcompletely the Biomechanical Status of Enzymatically Degraded Articular Cartilage at 9.4T".

Nishii et al., "Three dimensional Evaluation of the acetabular and femoral articular cartilage in the osteoarthritis of the Hip joint".

Parkkinen et al., "A mechanical apparatus with microprocessor controlled stress profile for cyclic compression of cultured articular cartilage explants," *J Biomech.* 1989;22(11–12):1285–91.

Pilch et al., "Assessment of cartilage volume in the femorotibial joint with magnetic resonance imaging and 3D computer resonstruction," *J. Rheumatol.* 21(12):2307–2321, 1994.

Potter et al., "Sensitivity of Quantitative NMR Imaging to Matrix Composition in Engineered Cartilage Tissue".

Probst et al., "Technique for measuring the area of canine articular surfaces," *Am. J. Vet. Res.* 48(4):608–609, 1987.

Reiser et al., "Magnetic resonance in cartilaginous lesions of the knee joint with three–dimensional gradient–echo imaging," *Skeletal Radiol.* 17(7):465–471, 1988.

Robarts Research Institute, Abstract #1028.

Robson et al., "A combined analysis and magnetic resonance imaging technique for computerized automatic measurement of cartilage thickness in distal interphalangeal joint," *Magnetic Resonance Imaging* 13(5):709–718, 1995.

Shapiro et al., "In–Vivo Evaluation of Human Cartilage Compresion and Recovery using 1H and 23Na MRI".

Solloway et al., "The use of active shape models for making thickness measurements of articular cartilage from MR images," *Magn Reson Med.* Jun. 1997;37(6):943–52.

Stammberger et al., "A New Method for 3D Cartilage Thickness Measurement with MR1, Based on Euclidean Distance Transformation, and its Reproducibility in the Living".

Stammberger et al., "Elastic registration of 3D cartilage surfaces from MR image data for detecting local changes of the cartilage thickness," *Magnetic Resonance in Medicine* 44: 592–601 (2000).

Stammberger et al., "A method for quantifying time dependent changes in MR signal intensity of artivular cartilage as a function of tissue deformation in intact joints," *Medical Engineering & Physics* 20:741–749, 1998.

Tebben et al., "Three–dimensional computerized reconstruction. Illusration of incremental articula cartilage thinning," *Invest. Radiol.* 32(8):475–484, 1997.

Vande Berg et al., "Assessment of knee cartilage in cadavers with dual–detector spiral CT arthrography and MR imaging," *J. Radiology.* Feb. 2002; 222(2):430–436.

Velyvis et al., "Evaluation of Articular Cartilage with Delayed Gd(DTPA)2–Enhanced MRI: Promise and Pitfalls".

Warfield et al., "Automation Segmentation of MRI of the Knee".

Warfield et al., "Adaptive template moderated spatially varying statistical classification," Proc. First International Conference on Medical Image Computing and Computer Assisted . . . , MICCAI 1998, pp. 231–238.

Warfield et al., "Adaptive, Template Moderated Spatially Varying Statistical Classification," *Medical Image Analysis* 4(1): 43–55, 2000.

Wayne et al., "Measurement of articular cartilage thickness in the articulated knee," *ANN Biomed Eng.* Jan.–Feb. 1998; 26(1):96–102.

Alexander E.J., "Estimating the motion of bones from markers on the skin (Doctoral Dissertation)," University of Illinois at Chicago (1998).

Alexander E.J. and Andriacchi, T.P., "Correcting for deformation in skin–based marker systems," Proceedings of the 3rd Annual Gait and Clinical Movement Analysis Meeting, San Diego, CA (1998).

Alexander E.J. and Andriacchi, T.P., "Internal to external correspondence in the analysis of lower limb bone motion," Proceedings of the 1999 ASME Summer Bioengineering Conference, Big Sky, Montana (1999).

Alexander E.J., and Andriacchi, T.P., "State estimation theory in human movement alalysis," Proceedings of the 1998 ASME International Mechanical Engineering Congress (1998).

Alexander et al., "Dynamic functional imaging of the musculoskeletal system," ASME Winter International Congress and Exposition, Nashville, Tennessee (1999).

Alexander et al., "Optimization techniques for skin deformation," Correction. International Symposium on 3–D Human Movement Conference, Chattanooga, TN, (1998).

Allen et al., "Late degenerative changes after meniscectomy 5 factors affecting the knee after operations," *J Bone Joint Surg* 66B:666–671 (1984).

Alley et al., "Ultrafast contrast–enhanced three dimensional MR Aagiography: State of the art," *Radiographics* 18:273–285 (1998).

Andriacchi, T.P., "Dynamics of Knee Malaligmnent," *Orthop Clin North Am* 25:395–403 (1994).

Andriacchi et al., "A point cluster method for in vivo motion analysis: Applied to a study of knee kinematics," *J. Biomech Eng* 120(12):743–749 (1998).

Andriacchi et al., "Methods for evaluating the progression of Osterarthritis," *Journal of Rehabilitation Research and Development* 37(2):163–170 (200).

Andriacchi and Strickland, "Gait analysis as a tool to assess joint kinetics biomechanics of normal and pathological human articulating joints," *Nijhoff, Series E* 93:83–102 (1985).

Andriacchi and Toney, "In vivo measurement of six–degrees–of–freedom knee movement during functional testing," *Transactions of the orthopedic Research Society* pp 698 (1995).

Beaulieu et al., "Glenohumeral relationships during physiological shoulder motion and stress testing: Initial experience with open MRI and active Scan–25 plane registration," *Radiology* (accepted for publication) (1999).

Beaulieu et al., "Dynamic imaging of glenohumeral instability with open MRI," *Int. Society for Magnetic Resonance in Medicine* Sydney, Australia (1998).

Bobic, V., "Arthoscopic osteochondral autograft transplantation in anterior cruciate ligament reconstruction: a preliminary clinical study," *Knee Surg Sports Traumatol Arthrosc* 3(4):262–264 (1996).

Boe S., and Hansen H., "Arthroscopic partial meniscectomy in patinets aged over 50," *J. Bone Joint Surg* 68B:707 (1986).

Bregler et al., "Recovering non–rigid 3D shape from image streams," *Proc.IEEE Conference on Computer Vision and Pattern Recognition* (2000) in press.

Brittberg et al., "A critical analysis of cartilage repair," *Acta Orthop Scand* 68 (2):186–191 (1997).

Brittberg et al., "Treatment of deep cartilage defects in the knee with autologous chondrocyte transplantation," *N Engl J Med* 331(14): 889–895 (1994).

Broderick et al., "Severity of articular cartilage abnormality in patients with osteoarthritis: evaluation with fast spin–echo MR vs arthroscopy," *AJR* 162: 99–103 (1994).

Butts et al., "Real–Time MR imaging of joint motion on an open MR imaging scanner," *Radiological Society of North America*, 83rd Scientific Assembly and Annual Meeting, Chicago, IL, (1997).

Daniel et al., "Breast cancer–gadolinium–enhanced MR imaging with a 0.5T open imager and three–point Dixon technique," *Radiology* 207(1):183–190 (1998).

Disler, D.G., "Fat–suppressed three–dimensional spoiled gradient–recalled MR imaging: assessment of articular and physeal hyaline cartilage," *AJR* 169:1117–1123 (1997).

Disler et al., "Fat–suppressed three–dimensional spoiled gradient–echo MR imaging of hyaline cartilage defects in the knee: comparison with standard MR imaging and arthroscopy," *AJR* 167:127–132 (1996).

Disler et al., "Detection of knee hyaline cartilage defects using fat–suppressed three–dimensional spoiled gradient–echo MR imaging: comparison with standard MR imaging and correlation with arthroscopy," *AJR* 165:377–382 (1995).

Doherty M, Hutton C, Bayliss MT: Osteoarthritis. In: Maddison PJ, Isenberg DA, Woo P, et al., eds. Oxford Textbook of Rheumatology, vol. 1. Oxford, New York, Tokyo: Oxford University Press, 959–983 (1993).

Dougados et al., "Longitudinal radiologic evaluation of osteoarthritis of the knee," *J Rheumatol* 19:378–384 (1992).

Du et al., "Vessel enhancement filtering in three–dimensional MR angiography," *J. Magn Res Imaging* 5:151–157 (1995).

Du et al., "Reduction of partial–volume artifacts with zero filled interpolation in three–dimensional MR Angiography," *J Magn Res Imaging* 4:733–741 (1994).

Dumoulin et al., "Real–time position monitoring of invasive devices using magnetic resonance," *Magn Reson Med* 29:411–5 (1993).

Eckstein et al., "In vivo reproducibility of three–dimensional cartilage volume and thickness measurements with MR imaging," *AJR* 170(3): 593–597 (1998).

Elting and Hubbell, "Unilateral frame distraction: proximal tibial valgus osteotomy for medial gonarthritis," *Contemp Orthop* 27(6):522–524 (1993).

Falcão et al., "User–steered image segmentation paradigms: Live wire and live lane," *Graphical Models and Image Processing* 60:233–260 (1998).

Felson et al., "Weight Loss Reduces the risk for symptomatic knee osteoarthritis in women: the Framingham study," *Ann Intern Med* 116:535–539 (1992).

Garrett, J.C., "Osteochondral allografts for reconstruction of articular defects of the knee," *Instr Course Lect* 47:517–522 (1998).

Ghosh et al., "Watershed segmentation of high resolution articular cartilage image," *International Society for Magnetic Resonance in Medicine*, Philadelphia, (1999).

Gouraud, H., "Continuous shading of curved surfaces," IEEE Trans on Computers C–20(6) (1971).

Hargreaves et al., "Technical considerations for DEFT imaging," *International Society for Magnetic Resonance in Medicine*, Sydney, Australia, Apr. 17–24, (1998).

Hargreaves et al., "Imaging of articular cartilage using driven equilibrium," International Society for Magnetic Resonance in Medicine, Sydney, Australia, Apr. 17–24, (1998).

Hayes and Conway, "Evaluation of Articular Cartilage: Radiographic and Cross–Sectional Imaging Techniques," *Radiographics 12*:409–428 (1992).

Henkelman et al., "Anisotropy of NMR properties of tissues," *Magn Res Med. 32*:592–601 (1994).

Hyhlik–Durr et al., "Precision of Tibial Cartilage Morphometry with a coronal water–excitation MR sequence," *European Radiology* 10 (2):297–303 (2000).

Irarrazabal et al., "Fast three–dimensional magnetic resonance imaging," *Mag Res. Med. 33*:656–662 (1995).

Johnson et al., "The distribution of load across the knee. A comparison of static and dynamic measurements," *J. Bone Joint Surg 62B*:346–349 (1980).

Johnson, T.S., "In vivo contact kinematics of the knee joint: Advancing the point cluster technique," Ph.D. Thesis, University of Minnesota (1999).

Johnson et al., "Development of a knee wear method based on prosthetic in vivo slip velocity," Transactions of the Orthopedic Research Society, 46th Annual Meeting, Mar., 2000.

Kass et al., "Snakes: Active contour models.," *Int J Comput Vision 1*:321–331 (1988).

LaFortune et al., "Three dimensional kinematics of the human knee during walking," *J. Biomechanics 25*:347–357 (1992).

Lang et al., "Functional joint imaging: a new technique integrating MRI and biomotion studies," *International Society for Magnetic Resonance in Medicine*, Denver, Apr. 18, 2000–Apr. 24, 2000 (2000).

Lang et al., Risk factors for progression of cartilage loss: a longitudinal MRI study. European Society of Musculoskeletal Radiology, 6th Annual Meeting, Edinburgh, Scotland, (1999).

Lang et al., Cartilage imaging: comparison of driven equilibrium with gradient–echo, SPAR, and fast spin–echo sequences. International Society for Magnetic Resonance in Medicine, Sydney, Australia, Apr. 17–24, (1998).

Ledingham et al., "Factors affecting radiographic progression of knee osteoarthritis," *Ann Rheum Dis 54*: 53–58 (1995).

Lorensen et al., "Marching cubes: a high resolution 3d surface construction algorithm," *Comput Graph 21*:163–169 (1987).

Losch et al., "A non–invasive technique for 3–dimensional assessment of articular cartilage thickness based on MRI part 1:development of a computational method," *Magn Res Imaging 15*(7):795–804 (1997).

Lu et al., "Bone position estimation from skin marker co–ordinates using globals optimization with joint constraints," *J Biomechanics 32*:129–134 (1999).

Lucchetti et al., "Skin movement artefact assessment and compensation in the estimation of knee–joint kinematics," *J Biomechanics 31*:977–984 (1998).

Lynch et al., "Cartilage segmentation of 3D MRI scans of the osteoarthritic knee combining user knowledge and active contours," Proc. SPIE 3979 Medical Imaging, San Diego, Feb. 2000.

Maki et al., "SNR improvement in NMR microscopy using DEFT," *J Mag Res* (1988).

Meyer et al., "Simultaneous spatial and spectral selective excitation," *Magn Res Med 15*:287–304 (1990).

Mollica et al., "Surgical treatment of arthritic varus knee by tibial corticotomy and angular distraction with an external fixator," *Ital J Orthop Traumatol* 18 (1):17–23 (1992).

Nizard, R.S., "Role of tibial osteotomy in the treatment of medial femorotibial osteoarthritis," *Rev Rhum Engl Ed 65*(7–9):443–446(1998).

Noll et al., "Homodyne detection in magnetic resonance imaging," IEEE Trans Med Imag 10(2):154–163 (1991).

Ogilvie–Harris et al., "Arthroscopic management of the degenerative knee," Arthroscopy 7:151–157 (1991).

Pearle et al., "Use of an external MR–tracking coil for active scan plane registration during dynamic Muscoloskeletal MR imaging in a vertically open MR unit," American Roentgen Ray Society, San Francisco, CA, (1998).

Peterfy et al., "Quantification of the volume of articular cartilage in the carpophalangeal joints of the hand: accuracy and precision of three–dimensional MR imaging," *AJR 165*: 371–375 (1995).

Peterfy et al., "MR imaging of the arthritic knee: improved discrimination of cartilage, synovium, and effusion with pulsed saturation transfer and fat–suppressed TI–weighted sequences," *Radiology 191*(2):413–419 (1994).

Peterfly et al.,"Quantification of articular cartilage in the knee with pulsed saturation transfer subtraction and fat–suppressed MR imaging: optimization and validation," *Radiology 192*(2): 485–491 (1994).

Piplani et al., "Articular cartilage volume in the knee: semiautomated determination from three–dimensional reformations of MR images," *Radiology 198*:855–859 (1996).

Potter et al., "Magnetic resonance imaging of articular cartilage in the knee: an evalution with use of fast–spin–echo imaging," *J. Bone Joint Surg 80–A*(9):1276–1284 (1998).

Prodromos et al., "A relationship between gait and clinical changes following high tibial osteotomy," *J. Bone Joint Surg 67A*:1188–1194 (1985).

Radin et al., "Mechanical Determination of Osteoarthrosis," *Sem Arthr Rheum 21*(3):12–21 (1991).

Radin et al., Characteristics of Joint Loading as it Applies to Osteoarthrosis in: Mow VC, Woo S.Y., Ratcliffe T., eds. Symposium on Biomechanics of Diarthrodial Joints, vol. 2, New York, NY: Springer–Verlag 437–451 (1990).

Recht et al., "Accuracy of fat–suppressed three–dimensional spoiled gradient–echo FLASH MR imaging in the detection of patellofemoral articular cartilage abnormalities,". *Radiology 198*:209–212 (1996).

Recht et al., "MR imaging of articular cartilage: current status and future directions," *AJR 163*:283–290 (1994).

Ritter et al., "Postoperative alignment of total knee replacement," *Clin Orthop 299*: 153–156 (1994).

Saito et al., "New algorithms for Euclidean distance transformation of an—dimensional digitized picture with applications," *Pattern Recognition 27* (11):1551–1565 (1994).

Schipplein and Andriacchi, "Interaction between active and passive knee stabilizers during level walking," *J. Orthop Res* 9:113–119. 199 1.

Schouten et al., "A 12 year follow up study in the general population on prognostic factors of cartilage loss in osteoarthritis of the knee," *Ann Rheum Dis 51*:932–937 (1992).

Sharif et al., "Serum hyaluronic acid level as a predictor of disease progression osteoarthritis of the knee," *Arthritis Rheum 38*:760–767 (1995).

Sharma et al., "Knee adduction moment, serum hyaluronic acid level, and disease severity in medial tibiofemoral osteoarthritis," *Arthritis and Rheumatism 41*(7):1233–40 (1998).

Shoup et al., "The driven equilibrium Fourier transform NMR technique: an experimental study," *J Mag Res* p.8 (1972).

Slemenda et al., "Lower extremity lean tissue mass and strength predict increases in pain and in functional impairment in knee osteoarthritis," *Arthritis Rheum* 39(suppl):S212 (1996).

Slemenda et al., "Lower extremity strength, lean tissue mass and bone density in progression of knee osteoarthritis," *Arthritis Rheum* 39(suppl):S169 (1996).

Solloway et al., "The use of active shape models for making thickness measurements of articular cartilage from MR images," *Mag Res Med* 37:943–952 (1997).

Spoor and Veldpas, "Rigid body motion calculated from spatial coordinates of markers," *J. Biomechanics* 13:391–393 (1980).

Stammberger et al., "Determination of 3D cartilage thickness data from MR imaging: computational method and reproducibility in the living," *Mag Res Med* 41:529–536 (1999).

Stammberger et al., "Interobserver to reproducibility of quantitative cartilage measurements: Comparison of B–spline snakes and manual segmentation," *Mag Res Imaging* 17:1033–1042 (1999).

Steines, D., et al., Segmentation of osteoarthritic femoral cartilage using live wire, ISMRM Eight Scientific Meeting, Denver Colorado, 2000.

Steines et al., "Segmentation of osteoarthritis femoral cartilage from MR images," CARS—Computer–Assisted Radiology and Surgery, pp 578–583, San Francisco, (2000).

Steines et al., Measuring volume of articular cartilage defects in osteoarthritis using MRI. To be presented at ACR 64th Annual Scientific Meeting, Philadelphia, Oct. (2000).

Stevenson et al., "The fate of articular cartilage after transplantation of fresh and cyropreserved tissue–antigen––matched and mismatched osteochondral allografts in dogs," *J. Bone Joint Surg* 71(9):1297–1307 (1989).

Tieschky et al., "Repeatability of patellar cartilage thickness patterns in the living, using a fat–suppressed magnetic resonance imaging sequence with short acquisition time and three–dimensional data processing," *J. Orthop Res* 15(6):808–813 (1997).

Tomasi and Kanade , "Shape and motion from image streams under orthography—a factorization method," *Proc. Nat. Acad. Sci.* 90(21):9795–9802 (1993).

Tsai et al., "Application of a flexible loop–gap resonator for MR imaging of articular cartilage at 3.TO," International Society for Magnetic Resonance in Medicine, Denver, Apr. 18, 2000–Apr. 24, 2000 (2000).

Wang et al., "The influence of walking mechanics and time on the results of proximal tibial osteotomy," *J. Bone Joint Surg* 72A:905–909 (1990).

Waterton et al., "Diurnal variation in the femoral articular cartilage of the knee in young adult humans," *Mag Res Med* 43:126–132 (2000).

Woolf et al., "Magnetization transfer contrast: MR imaging of the knee," *Radiology* 179: 623–628 (1991).

Worring et al., "Digital curvature estimation. CVGIP," *Image Understanding* 58(3): p. 366–382 (1993).

Yan, C.H., "Measuring changes in local volumetric bone density," new approaches to quantitative computed tomography, Ph.D. thesis, 1998, Dept. of Electrical Engineering, Stanford University.

Yao et al., "Incidental magnetization transfer contrast in fast spin–echo imaging of cartilage;" *J. Magn Reson Imaging* 6(1):180–184 (1996).

Yao et al., "MR imaging of joints: analytic optimization of GRE techniques at 1.5 T," *AJR* 158(2):339–345 (1992).

Yasuda et al., "A 10 to 15 year follow up observation of high tibial osteotomy in media compartment osteoarthritis," *Clin Orthop* 282:186–195 (1992).

* cited by examiner

A.

B.

TECHNIQUE FOR MANIPULATING MEDICAL IMAGES

This application claims the benefit of U.S. provisional patent applications Ser. Nos. 60/232,637 and 60/232,639 both of which were filed on Sep. 14, 2000 and which applications are hereby incorporate by reference in their entireties herein.

BACKGROUND OF THE INVENTION

MR imaging is currently the most accurate technique for assessing the articular cartilage non-invasively in vivo. A large array of different pulse sequences can be used for imaging articular cartilage. However, at present, the diagnosis of cartilage loss is based mostly on qualitative, visual analysis by the radiologist. One of the major obstacles in evaluating patients with osteoarthritis has been the lack of accurate and reproducible quantitative image processing and analysis techniques for monitoring progression of cartilage loss and response to medical or surgical therapy.

Some investigators reported the use of three-dimensional reconstruction of the articular cartilage with subsequent volumetric quantification of the entire cartilage surface. In one study, cartilage was segmented from the surrounding tissues using a signal intensity based thresholding technique applied to magnetization transfer subtraction images or fat-saturated T1-weighted images [1]. Since some of the adjacent tissues demonstrated signal intensity values overlapping those of articular cartilage, additional manual disarticulation of the cartilage was performed on selected image slices. Knees were imaged repeatedly. Cartilage volumes determined from the 3D reconstructions of MT subtraction and T1-weighted fat-saturated images were correlated to values obtained with water displacement of surgically retrieved tissue. They reported an intra-observer reproducibility error of 0.20–0.65 mL (3.6%–6.4%) for MT subtraction imaging and 0.21–0.58 mL (4.2%–6.4%) for T1-weighted fat-saturated imaging [1]. Inter observer error was less than 0.62 mL and 7.8%. In a subsequent study involving the metacarpophalangeal joints, they found a reproducibility error of 5.2% (95% confidence interval 2.9% to 7.6%) for metacarpal cartilage and 9.9% (5.4% to 15.1%) for proximal phalangeal cartilage [2]. They concluded that three-dimensional data analysis of MR images allows reproducible volumetric quantification of articular cartilage in the knee and metacarpophalangeal joints.

Piplani et al. refined this approach by combining signal intensity based thresholding of the articular cartilage with a connected-components or seed growing algorithm thereby obviating the need for manual disarticulation of the cartilage in those areas where adjacent tissues demonstrated overlapping signal intensities [3].

Stammberger et al. used B-spline snakes for semi-automated segmentation of articular cartilage [4]. A continuous and smooth parametric curve that depends on a number of control points is fit around the object by means of minimizing different energy terms. These energy terms control the smoothness of the curve and its attraction to certain image features, e.g. high graylevel gradients, causing it to act much like a rubber band.

Lynch et al. demonstrated a variation of the snake algorithm, in which the spline is adjusted to minimize costs calculated from Gauss and Canny filter responses [5]. The user initializes the system by selecting different control points in the medial and lateral tibio-femoral and the patello-femoral compartments. These control points are subsequently automatically adjusted as far as possible.

However, at present, there are no techniques available that perform reliably when used for segmentation of cartilage affected by advanced osteoarthritis. In these cases, MR images typically show a high degree of texture inhomogeneity of the cartilage, irregular and interrupted contours, and low contrast between the cartilage and surrounding tissue. These situations require a different technique for segmentation of the cartilage.

We developed a system for the calculation of the 3-dimensional cartilage thickness that is based on a 3D Euclidian distance transformation (EDT). For a given set of feature points in a binary volume, the EDT computes the distance to the closest feature point for each non-feature point of the volume. By using the points on the cartilage-bone interface (inner cartilage surface, ICS) as feature points, the EDT measures the distance to the closest voxel on the ICS for all other points, including the ones on the outer cartilage surface (OCS), resulting in a truly three-dimensional distance value determined normal to the ICS.

SUMMARY OF THE INVENTION

The general purpose of the invention and the embodiments described in this invention is to provide new techniques for extracting tissues from medical images. These techniques can be applied to diagnosing arthritis and for monitoring disease progression or response to therapeutic intervention.

In one embodiment, the invention provides for means to estimate the volume of cartilage layers in articular joints such as the knee joint using magnetic resonance imaging (MRI) scans. In another embodiment, the invention provides for means to estimate the thickness distribution of articular cartilage layers using an MRI scan. In another embodiment, the invention provides for means to measure volume and thickness distribution of specific volumes of interest (VOIs) in an MRI scan. In another embodiment, the invention provides for means to compare baseline and follow-up MRI scans of a patient. In another embodiment, the invention provides for means to identify the articular cartilage in an image, such as an MRI. In another embodiment, the invention provides for means to extract the articular cartilage from medical images for analysis purposes.

PREFERRED EMBODIMENTS

Figure 1:
FIG. 1 demonstrates a 2D MRI (3D spoiled gradient echo. The 2D MRI demonstrates a full thickness cartilage defect in the posterior lateral femoral condyle (arrows), as well as texture inhomogeneity.

In one embodiment the invention provides for a method of manipulating an image which method comprises extracting a tissue from said image wherein said extraction is facilitated with use of knowledge of the thickness, curvature, shape, dimensions or contour of said tissue. The tissue that can be extracted in the fashion can be bone or cartilage.

In another embodiment of the invention, knowledge of the thickness, curvature, shape, dimensions or contour of said tissue can be obtained from other subjects. These subjects can be age and sex matched with the patient. These subjects can be weight matched. These subjects can also have similar medical histories, for example a tear of the anterior cruciate ligament.

In another embodiment of the invention, knowledge of the thickness, curvature, shape, dimensions or contour of said tissue can be obtained from a reference database. This reference database can have bee generated in other age, sex, weight, or race matched individuals. Individuals can also have similar medical histories, for example a tear of the medial meniscus.

In another embodiment of the invention, knowledge of the thickness, curvature, shape, dimensions or contour of said tissue can be obtained from information derived from the same subject. For example, in segmenting arthritic or normal cartilage in a medical image, said information can be cartilage thickness, cartilage curvature or cartilage shape in a contralateral joint. Alternatively, said information on cartilage thickness, cartilage curvature or cartilage shape can be obtained in the same joint.

In another embodiment, the thickness, curvature, shape, dimensions or contour of another tissue, preferably a tissue adjacent to the tissue of interest, can be used to facilitate the segmentation or extraction of the tissue of interest. For example, in segmenting arthritic or normal cartilage in a medical image, the shape or contour of the subchondral bone can provide an estimate of the expected contour of the articular cartilage.

In another embodiment of the invention, knowledge of the thickness, curvature, shape, dimensions or contour of said tissue can be used to verify plausibility and correctness of the manipulation or segmentation of said tissue. For example, in segmenting normal cartilage in a medical image, a cartilage thickness or dimensions calculated from the segmentation that far exceed reference values from other patients matched by weight and height or values calculated from a baseline exam are likely to be incorrect.

In another embodiment, 2D MRI images can be used to create a 3D map of the articular cartilage thickness using color coding (or other means) to map thickness on a pixel-by-pixel basis. This can be displayed, for example, along the 3D surface of the articular cartilage.

This invention can be applied to any joint in a human or mammal, for example a knee joint or a hip joint. This invention can be particularly useful in humans suffering from arthritis and cartilage loss.

Another aspect of the invention is a method for assessing the condition of cartilage in a joint of a human, which method comprises (a) electronically transferring an electronically-generated image of a cartilage of the joint from a transferring device to a receiving device located distant from the transferring device;
(b) receiving the transferred image at the distant location;
(c) extracting said cartilage from said transferred image
(d) converting the transferred image to a normal or degeneration pattern of the cartilage;
(e) storing said normal or degeneration pattern of cartilage in a database, and
(f) transmitting said normal or said degeneration pattern to a site for analysis.

The information stored in the database on said normal and degeneration patterns can be used to facilitate said extraction of cartilage from said transferred images in other patients or to verify plausibility and correctness of said extraction of cartilage from said transferred images in other patients.

Another aspect of the invention is a method for assessing the condition of cartilage in a joint of a human, which method comprises (a) extracting said cartilage from said image
(b) electronically transferring an electronically-generated image of said extracted cartilage of the joint from a transferring device to a receiving device located distant from the transferring device;
(c) receiving the transferred image at the distant location;
(d) converting the transferred image to a normal or degeneration pattern of the cartilage;
(e) storing said normal or degeneration pattern of cartilage in a database, and
(f) transmitting said normal or said degeneration pattern to a site for analysis.

The information stored in the database on said normal and degeneration patterns can be used to facilitate said extraction of cartilage from said transferred images in other patients or to verify plausibility and correctness of said extraction of cartilage from said transferred images in other patients.

The live wire algorithm that was introduced by Falcão [6] can provide a flexible general framework well-suited for adaptation for the purpose of segmenting osteoarthritic cartilage. It can evaluate different features of the oriented edges between two pixels (boundary element, bel) and finally can calculate a single cost value for every bel based on these features. For a starting pixel P that is selected by the user with the mouse, the system can calculate the bel path with the least sum of costs from each image pixel to P. When the user moves the mouse cursor, the system can now draw the calculated path from the current mouse position. The current path can be frozen as part of the object contour by the user. Thus, the object contour is assembled from a number of live wire segments.

The live wire algorithm as presented by Falcão et al. is, however, too general to be effective in the segmentation of osteoarthritic cartilage. The current invention can be used to enhance and extend the live wire algorithm, thus providing for means to efficiently segment cartilage from MR images in patients with severe osteoarthritis.

In one embodiment of the invention, a live wire technique can be used to segment the cartilage. Various features can be used alone or in combination to help segment the articular cartilage with the live wire technique. Such features include, but are not limited to:
1. Grayvalue of the pixel on the left side of the bel
2. Grayvalue of the pixel on the right side of the bel
3. Magnitude of the graylevel gradient across the bel
4. Distance of the closest bel in the previously segmented slice For example, the distance of the outer cartilage surface (OCS) to the inner cartilage surface (ICS) can be used as an aid in segmenting the cartilage.

Figure 2:
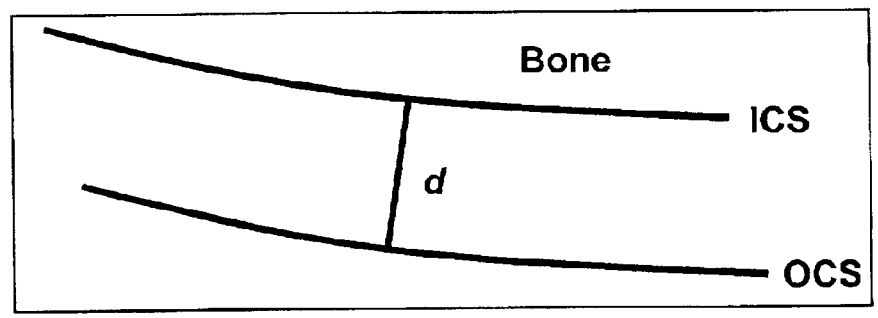
FIG. 2 demonstrates the distance d between the inner cartilage surface (ICS) and the outer cartilage surface (OCS), as used, for example, for the new live wire feature.

Prior knowledge that femoral cartilage, for example, usually does not exceed a thickness of approximately 4 mm can be used with this feature. If the cartilage-bone interface (ICS) is segmented first in a slice, which can usually be easily done on sagittal MR images due to high contrast between bone and cartilage, this information can be helpful in regions of low contrast between OCS and surrounding tissue. The feature value is the distance of the bel to the closest bel on the ICS (see FIG. 2). For distance calculation, a Euclidean distance transform algorithm can be used. The cost can be calculated with a modified hyperbolic function that increases from 0 to 1 above a thickness value taken from a reference database. This feature can prevent the OCS contour from moving too far away from the ICS contour.

In another embodiment of the invention, the direction of the graylevel gradient of the OCS compared with the gradient of the corresponding section of the ICS can be used to help in segmenting the cartilage.

Except in the periphery of the cartilage where the ICS and the OCS meet and in regions of defective cartilage the OCS is usually approximately parallel to the ICS. This knowledge can be used to combine magnitude and direction of the graylevel gradient in order to help finding the contour in regions of low contrast between the OCS and surrounding tissue. If b is a boundary element under consideration for the OCS and c the closest bel on the previously segmented ICS, and $\vec{\beta}$ and $\vec{\gamma}$ are the vectors of the graylevel gradient across b and c, the value $f$ for this feature can be computed as follows:

$$f = \frac{1}{|\vec{\beta}|} \cdot \left( 1 - \left| \frac{\vec{\beta} \cdot \vec{\gamma}}{|\vec{\beta}| \cdot |\vec{\gamma}|} \right| \right) \tag{1}$$

In this equation, the first factor is the inverse of the gradient magnitude across b. The second factor includes the absolute value of the cosine of the angle $\vec{\psi}$ between $\beta$ and $\vec{\gamma}$ and has a low value when the vectors are nearly parallel since $|Cos\psi|$ is close to 1. Thus, the lower the gradient magnitude across b, the more weight is given to its direction. The cost function is a linear mapping within a predetermined interval I of feature values. Values outside of are mapped to 1.

Figure 3:
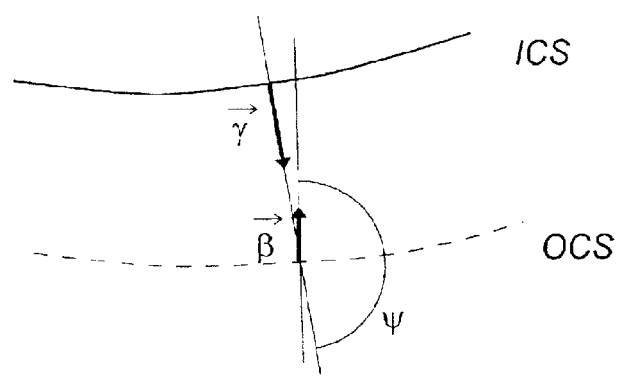
FIG. 3 shows a schematic of the use of an aspect of the invention, in this example used with the Live Wire algorithm. A low contrast between OCS and surrounding tissue; bel b has low cost since gradients $\vec{\beta}$ and $\vec{\gamma}$ are almost parallel. B. High contrast between OCS and surrounding tissue; b has low cost due to high magnitude of gradient $\beta$.
Figure 3:
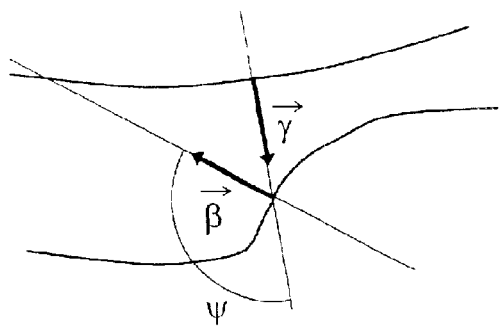

Thus, within I the cost for b increases with increasing deviation of the direction of gradient $\vec{\beta}$ from the direction of the gradient on the opposing ICS. A high degree of parallelism between $\vec{\beta}$ and $\vec{\gamma}$ results in a high probability of b being included in the contour (see FIG. 3A). In effect, this means that the ICS is taken as a template for the OCS where the OCS is not clearly recognizable. In areas of high contrast between the OCS and surrounding tissue, however, this is not necessary, so that the gradient direction can be weighted less (see FIG. 3B). This also makes the detection of cartilage defects possible.

In another embodiment, different boundary element features may be considered together. Their relative weighting can be the same for each slice or can be changed depending on regional variations in one or more of these features.

The invention provides for means to reliably segment articular cartilage from MR images that has been damaged due to advanced osteoarthritis. In one embodiment, the invention will be used to determine the total volume of an articular cartilage layer.

In another embodiment, the invention will be used to calculate the 3-dimensional thickness distribution of an articular cartilage layer.

In another embodiment, the invention will be used to calculate a volume of interest that is targeted over an area of diseased cartilage rather than including the entire surface of the articular cartilage.

In another embodiment, the invention provides for means to compare baseline and follow-up studies of a patient. This will be done by segmenting the articular cartilage in both studies using the invention, and subsequently registering the segmented cartilage objects by means of a surface registration technique.

In another embodiment, the invention provides means to verify plausibility and correctness of said thickness and volume calculations.

The techniques provided in this invention provide means to accurately and reliably extract cartilage from medical images. For example, the techniques described in this invention provide means to accurately and reliably segment cartilage from MR scans that has been destroyed or deformed due to osteoarthritis. Existing cartilage segmentation methods do not perform reliably and accurately in case of diseased cartilage. The invention improves the diagnostic capabilities of cartilage quantification methods that can be used for the assessment of arthritis, for example in patients undergoing treatment with a chondroprotective or a chondroregenerative agent. The invention also facilitates the segmentation process for the user, thus reducing the amount of time necessary to segment cartilage from the MR or other medical images.

Someone skilled in the art will easily recognize other means of practicing the invention. For example, the specific cost mapping functions used to calculate the feature costs, and its parameters can be easily modified. Variations of formula 1, leading to similar results, are evident.

EXAMPLES

The examples below are exemplary of how aspects of the invention can be practiced. The examples are in no way meant to be limiting of the invention. Someone skilled in the art will easily recognize other means of practicing the invention.

In one example, a live wire algorithm is used for segmentation of osteoarthritic cartilage. Several features can be used alone or in combination to help segment the articular cartilage with the live wire technique. The features in this example include:

1. the grayvalue of the pixel on the left side of the bel
2. the grayvalue of the pixel on the right side of the bel
3. the magnitude of the graylevel gradient across the bel
4. the distance of the closest bel in the previously segmented slice
5. the distance of the outer cartilage surface (OCS) to the inner cartilage surface (ICS).

Prior knowledge that femoral cartilage, for example, usually does not exceed a thickness of approximately 4 mm can be used with this feature. The feature value is the distance of the bel to the closest bel on the ICS (see FIG. 2). For distance calculation, a Euclidean distance transform algorithm can be used. The cost is calculated with a modified hyperbolic function that increases from 0 to 1 above a reference thickness value. This feature can prevent the OCS contour from moving too far away from the ICS contour.

Listing of Preferred Embodiments of the Invention

As will be apparent to those of skill in the arts to which the current invention pertains, there are numerous elements involved in the practice of the invention, and those elements can be combined in different manners to provide multiple embodiments of the invention. A non-exhaustive list of preferred embodiments is provided to exemplify practice of the invention. This list is primarily directed to medical applications, particularly those that relate to the determination of the outer cartlidge surface of an articular joint, as determination of such a surface from a digital image is a particularly difficult challenge for which the present invention is well suited.

1. A method of manipulating an image which method comprises
   a. determining the gray value of a pixel on the left side of a boundary element
   b. determining the gray value of a pixel on the right side of a boundary element
   c. determining the magnitude of the graylevel gradient across the boundary element
   d. determining the distance of the closest boundary element in the previously manipulated image slice, whereby determining the distance of the closest boundary element in the previously manipulated image slice improves the accuracy of the manipulation.

2. The method of embodiment 1 wherein the image is an MRI and the method is used to locate the bone cartilage interface.
3. The method of embodiment 1 wherein the image is an MRI and the method is used to locate the external cartilage surface.
4. The method of embodiments 2 and 3 wherein the cartilage is normal.
5. The method of embodiments 2 and 3 wherein the cartilage is diseased.
6. A method of manipulating an image which method comprises extracting a tissue from the image wherein the extraction is facilitated with use of knowledge of the thickness, curvature, shape or contour of the tissue.
7. The method of embodiment 6 wherein the tissue is bone.
8. The method of embodiment 6 wherein the tissue is cartilage.
9. The method of embodiment 6 wherein the knowledge of the thickness, the curvature, or the contour is obtained from information derived from other subjects.
10. The method of embodiment 9 wherein the other subjects are age and sex matched with the patient.
11. The method of embodiment 9 wherein the other subjects are weight matched.
12. The method of embodiment 6 wherein the knowledge is obtained from information derived from the same subject.
13. The method of embodiment 6 wherein the information is cartilage thickness, cartilage curvature or cartilage shape in a contralateral joint.
14. The method of embodiment 6 wherein the information is cartilage thickness, cartilage curvature or cartilage shape in the same joint.
15. The method of embodiment 6 wherein the knowledge is curvature or shape of the bone in the same joint.
16. The method of embodiment 15 wherein the bone is subchondral bone.
17. The method of embodiment 16 wherein the curvature or the shape of the subchondral bone is used to estimate the curvature or shape of the overlying articular cartilage.
18. The method of embodiment 6 wherein the image is an image of the knee joint.
19. The method of embodiment 18 wherein the joint has arthritis.
20. The method of embodiment 19 wherein the arthritis has caused cartilage loss.
21. A method of manipulating an image which method comprises segmenting the image wherein the segmentation is facilitated with use of knowledge of an expected range of the thickness, curvature, shape, dimensions or contour of at least one tissue.
22. The method of embodiment 21 wherein the tissue is bone.
23. The method of embodiment 21 wherein the tissue is cartilage.
24. The method of embodiment 21 wherein the knowledge of the thickness, the curvature, the shape, the dimensions or the contour is obtained from information derived from other subjects.
25. The method of embodiment 24 wherein the other subjects are age and sex matched with the patient.
26. The method of embodiment 24 wherein the other subjects are weight matched.
27. The method of embodiment 21 wherein the knowledge is obtained from information derived from the same subject.
28. The method of embodiment 21 wherein the information is cartilage thickness, cartilage curvature, cartilage contour or cartilage shape in a contralateral joint.
29. The method of embodiment 21 wherein the information is cartilage thickness, cartilage curvature, cartilage contour or cartilage shape in th e same joint.
30. The method of embodiment 21 wherein the knowledge is curvature, contour or shape of at least one bone in the same joint.
31. The method of embodiment 30 wherein the bone is subchondral bone.
32. The method of embodiment 31 wherein the curvature, the contour or the shape of the subchondral bone is used to estimate the curvature, contour or shape of the overlying articular cartilage.
33. The method of embodiment 21 wherein the image is an image of the knee joint.
34. The method of embodiment 33 wherein the joint has arthritis.
35. The method of embodiment 34 wherein the arthritis has caused cartilage loss.
36. The method of embodiment 32 wherein the curvature, the contour or the shape of the subchondral bone is used to estimate the curvature, contour or shape of the overlying articular cartilage at the interface of the subchondral bone with the overlying articular cartilage.
37. The method of embodiment 32 wherein the curvature, the contour or the shape of the subchondral bone is used to estimate the curvature, contour or shape of the overlying articular cartilage at the external, articular surface.
38. A method of manipulating a medical image which method comprises
   a. determining the gray value of a pixel on the left side of a boundary element
   b. determining the gray value of a pixel on the right side of a boundary element
   c. determining the distance of a boundary element to the inner cartilage surface (ICS)

whereby the inner cartilage surface is located in the joint of a human and whereby determining the distance of the boundary element to the inner cartilage surface (ICS) improves the accuracy of the manipulation.

39. The method of embodiment 38 wherein the image is an MRI and the method is used to locate the outer cartilage surface.
40. The method of embodiment 39 wherein the cartilage is normal.
41. The method of embodiment 39 wherein the cartilage is diseased.
42. The method of embodiment 38 wherein the manipulation includes a live wire algorithm.
43. The method of embodiment 42 wherein the live wire algorithm uses a cost function that employs a modified hyperbolic function that increases from 0 to 1 when the distance from the inner cartilage surface to the outer cartilage surface increases above a reference value in the femoral condyles.

44. The method of embodiment 42 wherein the live wire algorithm uses a cost function that employs a modified hyperbolic function that increases from 0 to 1 when the distance from the inner cartilage surface to the outer cartilage surface increases above a reference value in the tibial plateau.

45. The method of embodiment 42 wherein the live wire algorithm uses a cost function that employs a modified hyperbolic function that increases from 0 to 1 when the distance from the inner cartilage surface to the outer cartilage surface increases above a reference value in the patella.

46. The method of embodiment 38 wherein the manipulation includes a snake algorithm.

47. A method of manipulating an image which method comprises
   a. determining the gray value of a pixel on the left side of a boundary element
   b. determining the gray value of a pixel on the right side of a boundary element
   c. determining the distance of the closest boundary element in the previously manipulated image slice,
   whereby determining the distance of the closest boundary element in the previously manipulated image slice improves the accuracy of the manipulation.

48. The method of embodiment 47 wherein the image is an MRI and the method is used to locate the bone cartilage interface.

49. The method of embodiment 47 wherein the image is an MRI and the method is used to locate the external cartilage surface.

50. The method of embodiments 48 and 49 wherein the cartilage is normal.

51. The method of embodiments 48 and 49 wherein the cartilage is diseased.

52. A method for assessing the condition of cartilage in a joint of a human, which method comprises
   (a) electronically transferring an electronically-generated image of a cartilage of the joint from a transferring device to a receiving device located distant from the transferring device;
   (b) receiving the transferred image at the distant location;
   (c) extracting the cartilage from the transferred image
   (d) converting the transferred image to a normal or degeneration pattern of the cartilage; and
   (e) transmitting the normal or the degeneration pattern to a site for analysis.

53. The method of embodiment 52 wherein the normal or the degeneration pattern is stored in a database.

54. The method of embodiment 53 wherein the database can be used to facilitate the extraction of the cartilage from the transferred images in other patients.

55. The method of embodiment 53 wherein the database contains information on subjects' age, sex, race, weight or medical condition.

56. The method of embodiment 52 wherein after step (e), the degeneration pattern is displayed as a three-dimensional image.

57. The method of embodiment 56 wherein the joint is a knee joint.

58. The method of embodiment 52, 56 or 57 wherein all steps are carried out at an initial time (T1) and are carried out again at a later time (T2).

59. The method of embodiment 58 wherein the assessment includes an analysis of the degree of degeneration of the cartilage between T1 and T2.

60. The method of embodiment 52 wherein the electronically-generated image of a cartilage is obtained by a magnetic resonance imaging (NWI technique.

61. A method of embodiment 60, wherein the MRI technique provides a biochemical description of the cartilage.

62. A method of embodiment 60, wherein the NMI technique provides a volumetric description of the cartilage.

63. The method of embodiment 60 wherein the MRI technique results in a three-dimensional image of the cartilage.

64. The method of embodiment 63 wherein the MRI technique first obtains a series of two-dimensional views of the joint, which are then mathematically integrated to give a three-dimensional image.

65. The method of embodiment 60 wherein the MRI technique employs a gradient echo, spin echo, fast-spin echo, driven equilibrium fourier transform, or spoiled gradient echo technique.

66. The method of embodiment 60, wherein the assessment of the condition of cartilage in a joint of a human is followed by one or more assessments of the condition of the same cartilage at a later point in time.

67. A method for assessing the condition of cartilage in a joint of a human, which method comprises
   (a) extracting the cartilage from an electronically-generated medical image
   (b) electronically transferring the electronically-generated image of a cartilage of the joint from a transferring device to a receiving device located distant from the transferring device;
   (c) receiving the transferred image at the distant location;
   (d) converting the transferred image to a normal or degeneration pattern of the cartilage; and
   (e) transmitting the normal or the degeneration pattern to a site for analysis.

68. The method of embodiment 67 wherein the normal or the degeneration pattern is stored in a database.

69. The method of embodiment 68 wherein the database can be used to facilitate the extraction of the cartilage from the transferred images in other patients.

70. The method of embodiment 68 wherein the database contains information on subjects' age, sex, race, weight or medical condition.

71. The method of embodiment 67 wherein after step (e), the degeneration pattern is displayed as a three-dimensional image.

72. The method of embodiment 67 wherein the joint is a knee joint.

73. The method of embodiment 67, 71 or 72 wherein all steps are carried out at an initial time (T1) and are carried out again at a later time (T2).

74. The method of embodiment 73 wherein the assessment includes an analysis of the degree of degeneration of the cartilage between T1 and T2.

75. The method of embodiment 67 wherein the electronically-generated image of a cartilage is obtained by a magnetic resonance imaging (MRI) technique.

76. A method of embodiment 75, wherein the MRI technique provides a biochemical description of the cartilage.

77. A method of embodiment 75, wherein the MRI technique provides a volumetric description of the cartilage.

78. The method of embodiment 75 wherein the MRI technique results in a three-dimensional image of the cartilage.

79. The method of embodiment 78 wherein the MRI technique first obtains a series of two-dimensional views of the joint, which are then mathematically integrated to give a three-dimensional image.

80. The method of embodiment 75 wherein the MRI technique employs a gradient echo, spin echo, fast-spin echo, driven equilibrium fourier transform, or spoiled gradient echo technique.

81. The method of embodiment 75, wherein the assessment of the condition of cartilage in a joint of a human is followed by one or more assessments of the condition of the same cartilage at a later point in time.

Detailed Specific Example

Methods

Image Segmentation

Figure 4:
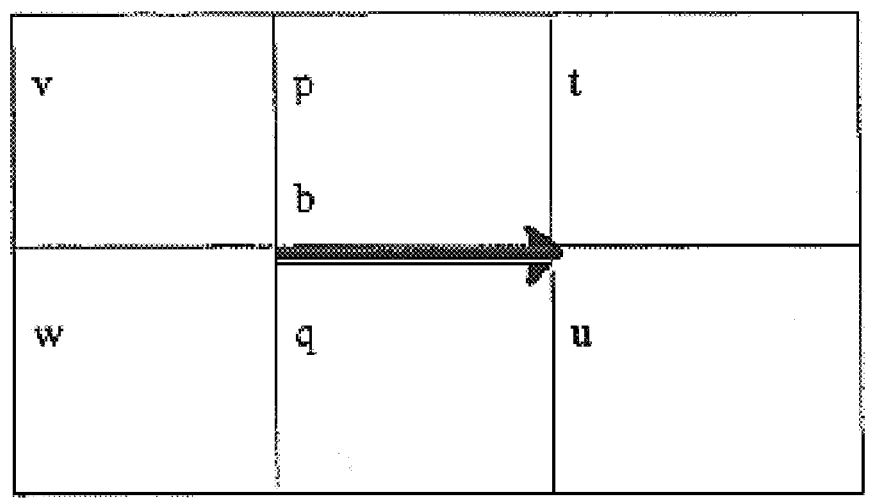
FIG. 4 shows a schematic of bel b and its neighborhood of pixels p, q, t, u, v, w.

The live wire algorithm finds the contours of an object by evaluation of a set of features for each boundary element. A boundary element (bel) is the oriented edge between two pixels (see FIG. 4). Using an individual cost function for each feature, the feature values are converted into cost values between 0 and 1. Finally, the weighted sum of all feature costs results in a single joint cost value between 0 and 1 for each bel b that expresses the likelihood of b being part of the cartilage boundary [6]. This determines whether the pixels on either side of the bel are assigned to one tissue or the other that form the boundary. To determine the contour of a cartilage object, the user chooses a starting pixel P with a mouse click. Subsequently, the system calculates the bel path with the least sum of costs from each image pixel to P using a dynamic programming scheme. When the user moves the mouse cursor, the system can now display the calculated path from the current mouse position to P in real time. The current path can be frozen as part of the cartilage contour by the user. Thus, the cartilage contour in each slice is assembled from a number of frozen live wire segments.

The live wire contour should be drawn around the cartilage in a consistent direction. In the following it is assumed that the direction has been chosen by the user such that the cartilage is always to the right of a bel. We are currently using the following boundary element features and cost functions:

1. Grayvalue of pixel p. The grayvalue of pixel p (see FIG. 4), which is supposed to lie outside the cartilage, is mapped to a cost value using an inverted Gaussian function with the mean and standard deviation as parameters that have to be chosen appropriately. Grayvalues close to the mean are converted to low cost values.

2. Grayvalue of pixel q: The same process is applied to pixel q, which is assumed to be a cartilage pixel. These features attract the contour to pixels with grayvalues close the chosen means.

3. Magnitude of the graylevel gradient across b is computed according to equation 2. The cost function is a thresholding function that is 0 inside and 1 outside a given interval. This prevents the contour from locking onto the cartilage-bone interface of the tibia when segmenting the femoral outer cartilage surface.

$$f = \frac{1}{2}\left|g(p) + \frac{1}{2}g(t) + \frac{1}{2}g(v) - g(q) - \frac{1}{2}g(u) - \frac{1}{2}g(w)\right| \quad (2)$$

4. Distance of b to closest bel in previously segmented slice: The contour is drawn towards a previously segmented contour in an adjacent slice. Thus, one carefully segmented slice can provide useful information for subsequent slices.

The distance is calculated by means of a fast Euclidean distance transform (EDT) algorithm [12]. The cost increases linearly with the distance.

5. Distance of outer cartilage surface (OCS) to inner cartilage surface (ICS): Prior knowledge that femoral cartilage, for example, typically does not exceed a thickness of approximately 4 mm [7] is incorporated as another feature. If the cartilage-bone interface (ICS) is segmented first in a slice, which can usually be easily done in sagittal MR images due to high contrast between bone and cartilage, this information is helpful in regions of low contrast between OCS and surrounding tissue. For distance calculation the same EDT algorithm as in feature 4 is used. The cost is calculated with a modified hyperbolic function that increases from 0 to 1 above 4 mm. This feature prevents the OCS contour from moving too far away from the ICS contour.

6. Direction of graylevel gradient of OCS compared with the gradient of the corresponding section of ICS Except in the periphery of the cartilage where the ICS and the OCS meet and in regions of defective cartilage the OCS is usually approximately parallel to the ICS. This knowledge is used to combine magnitude and direction of the graylevel gradient in order to help finding the contour in regions of low contrast between the OCS and surrounding tissue. The lower the gradient magnitude across a bel b on the OCS, the more weight is given to its direction. The cost for b increases with increasing deviation of the direction of its gradient $\vec{\beta}$ from the direction of the gradient $\vec{\gamma}$ on the opposing ICS. A high degree of parallelism between $\vec{\beta}$ and $\vec{\gamma}$ results in a high probability of b being included in the contour. In effect, this means that the ICS is taken as a template for the OCS where the OCS is not clearly recognizable, In areas of high contrast between the OCS and surrounding tissue, however, this is not necessary, so that the gradient direction can be weighted less. This also makes the detection of cartilage defects possible. To facilitate the selection of the Gaussian cost function parameters for the user, the images may be first processed with a Kuwahara smoothing filter with a 3×3 window size [13]. This non-linear filter reduces noise while preserving eges in the image.

Interobserver Reproducibility

In preliminary experiments interobserver reproducibility of the proposed method was assessed using sagittal MR images of the knee acquired from five, patients with different stages of osteoarthritis (1.5 T GE Signa, fat-saturated 3D SPGR, TE 5 ms, TR 60 ms, flip angle 40°, voxel size 1.5×47×47 mm$^3$). Three observers segmented the femoral cartilage with the live wire method, using features 1–3. Parameters measured from segmented data were total cartilage volume, maximum thickness, average thickness, and number of voxels on the OCS.

Thickness values were calculated using a 3-dimensional EDT [8, 12]. Interreader reproducibility was determined as the coefficient of variation (CV %) between the three, observers for each patient.

Results

An example of the processing steps for the cartilage segmentation is above. The contours of normal cartilage and areas of thinning and full thickness loss are correctly identified with the live wire technique The results of the interobserver reproducibility assessment are presented in Table

TABLE 1

Interobserver reproducibility (CV %). The average interobserver reproducibility is given as root mean square (RMS) of the CV %.

| Patient | Volume | Max. thickness | Avg. thickness | Surface voxels |
|---------|--------|----------------|----------------|----------------|
| A       | 4.7%   | 0.2%           | 3.8%           | 1.5%           |
| B       | 13.5%  | 7.6%           | 10.5%          | 2.7%           |
| C       | 8.6%   | 3.3%           | 6.7%           | 0.7%           |
| D       | 7.7%   | 4.9%           | 5.7%           | 3.1%           |
| E       | 5.9%   | 0.7%           | 5.8%           | 1.0%           |
| RMS     | 8.6%   | 4.3%           | 6.9%           | 2.0%           |

Discussion

The experiments on the interobserver reproducibility of segmentation of osteoarthritic femoral cartilage using the proposed live wire technique yielded approximately the same results as published for similar parameters obtained from healthy volunteers with the B-spline snake method [11]. However, as Table 1 also shows, the variation of values obtained for the total cartilage volume remains high. This is partially caused by difficulties to identify the correct cartilage boundaries in the peripheral regions of the femoral condyles where the sagittal imaging plane is nearly tangential to the cartilage surface, thus blurring the edges due to high partial volume effects.

In general, the live wire segmentation technique proved to provide the necessary flexibility for segmentation of osteoarthritic cartilage. New features can easily be implemented and included into the system. Subjectively, the technique greatly facilitates segmentation compared to manual delineation of the contours. Its principal advantage lies in the evaluation of local image features in a global context, which is important for the correct treatment of cartilage irregularities in segmentation.

Further improvements can be made by including methods for automatic determination of the cost function parameters from the images, which will additionally increase reproducibility. Thus, the present technique holds the potential to improve and facilitate semi-automatic segmentation of both normal and diseased cartilage.

REFERENCES

1. Peterfy, C. G., et al., *Quantification of articular cartilage in the knee with pulsed saturation transfer subtraction and fat-supressed MR imaging: optimization and validation*. Radiology, 1994.192(2): p. 485–491.
2. Peterfy, C. G., et al., *Quantification of the volume of articular cartilage in the metacarpophalangeal joints of the hand: accuracy and precision of three-dimensional MR imaging*. AJR, 1995.165: p. 371–375.
3. Piplani, M. A., et al., *Articular cartilage volume in the knee: semi-automated determination from three-dimensional reformations of MR images*. Radiology, 1996. 198(3): p. 855–859.
4. Stammberger, T., et al., *Interobserver reproducibility of quantitative cartilage measurements: Comparison of B-spline snakes and manual segmentation*. Magnetic Resonance Imaging, 1999. 17(7): p. 1033–1042.
5. Lynch, J. A., et al. *Cartilage segmentation of 3D MRI scans of the osteoarthritic knee combining user knowledge and active contours, in SPIE Medical Imaging.* 2000. San Diego.
6. Falcão, A. X., et al., *User-steered image segmentation paradigms: Live wire and live lane*. Graphical Models and Image Processing, 1998. 60: p. 233–260.
7. Swann, A. C. and B. B. Seedhom, *Improved techniques for measuring the indentation and thickness of articular cartilage*. Proc Inst Mech Eng, 1989. 203(3): p. 143–150.
8. T. Stammberger, F. Eckstein, K. H. Englmeier, and M. Reiser. Determination of 3D cartilage thickness data from MR imaging: Computational method and reproducibility in the living. *Magnet Reson Med,* 41:529–536, 1999.
9. S. Ghosh, D.C. Newitt, and S. Majumdar. Watershed segmentation of high resolution articular cartilage image. In *Proc. ISMRM*, page 1024, Philadelphia, 1999.
10. S. Solloway, C. E. Hutchinson, J. C. Waterton, and C. J. Taylor. The use of active shape models for making thickness measurements of articular cartilage from MR images. *Magnet Reson Med,* 37:943–952, 1997.
11. T. Stammberger, F. Eckstein, A. Michaelis, K. H. Englmeier, and M. Reiser. Interobserver reproducibility of quantitative cartilage measurements: Comparison of B-spline snakes and manual segmentation. *Magn Reson Imaging,* 17(7):1033–1042, 1999.
12. T. Saito and J A. Toriwaki. New algorithms for euclidian distance tranformation of an n-dimensional digitized picture with applications. *Pattern Recognition,* 27(11):1551–1565, 1994.
13. M. Kuwahara, K. Hachimura, S. Eiho, and M. Kinoshita. *Digital Processing of Biomedical Images*, Plenum Press, New York, 1976

The present invention is related to and can be used in combination with other inventions arising out of investigations in the laboratories of the present inventors, as well as in combination with many other independently developed or publically available techniques for the investigation and manipulation of digital images, particularly such images as they relate to medical images and the segmentation of tissues. Examples of applications related to the present invention that were developed in the laboratories of the present inventors can be found in the disclosures of the following patent documents:

PCT Publication No. WO 00/35346, published Jun. 22, 2000, entitled "Assessing the Condition of a Joint and Preventing Damage."

U.S. application Ser. No. 60/232,639, filed Sep. 14, 2000, entitled "New Techniques for Manipulating Medical Images."

U.S. application Ser. No. 60/232,637, entitled "Assessing the Condition of a Joint and Assessing Cartilage Loss."

U.S. application Ser. No. 09/662,224, entitled "Assessing the Condition of a Joint and Devising Treatment."

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

We claim:

1. A method of assessing a digital image to determine a boundary between first and second image components, which comprises:

(a) selecting a first boundary element between two pixels being evaluated for assignment to the first or second image component;

(b) determining a first value of a first pixel on one side of the first boundary element;

(c) determining a second value of a second pixel on the other side of the first boundary element;

(d) comparing the first and second value to determine magnitude of a gradient across the first boundary element and assigning a gradient boundary value to the first boundary element;

(e) determining relative locations of (1) the first boundary element and (2) a reference element selected from the group consisting of (2a) a reference boundary element previously assigned as separating a pixel assigned to the first image component from a pixel assigned to the second image component and (2b) a reference second-boundary element previously assigned as separating a pixel assigned to one of the first and second image components from a third image component, the second-boundary element having a known, statistically significant distance or angle relationship relative to an actual boundary between real components represented by the first and second image components, and assigning a location boundary value to the first boundary element based on distance or angle of the relative locations from each other;

(f) mathematically combining the gradient boundary value and the location boundary value to provide a first potential boundary value for the first boundary element; repeating steps (a)–(f) for a second boundary element to obtain a second potential boundary value; and (g) assigning the first boundary element or the second boundary element as dividing the first image component from the second image component, depending on relative potential boundary values of the first and second boundary elements, wherein said method is used to locate a bone/cartilage interface or an external cartilage surface.

2. The method of claim 1, wherein said image is a magnetic resonance image, an ultrasound image, or an X-ray image.

3. The method of claim 2, wherein said cartilage is diseased or damaged.

4. The method of claim 1, wherein said method assigns said boundary element to said first or second image component using existing knowledge of probable shape of said first or second image component.

5. The method of claim 4, wherein said digital image is of a living subject and said first and second image components comprise first and second tissues of said living subject.

6. The method of claim 5, wherein said knowledge is obtained from (a) information derived from same-type tissue images of other subjects or (b) information derived from a different image obtained from said living subject or from a different region of said tissue image.

7. The method of claim 6, wherein said other subjects are age and sex matched or weight matched with said living subject.

8. The method of claim 6, wherein said information is (a) cartilage thickness, cartilage curvature or cartilage shape in a contralateral joint or in a different region of a first joint whose image is being assessed or (b) curvature or shape of a bone in said first joint.

9. The method of claim 8, wherein said bone is subchondral bone.

10. The method of claim 9, wherein curvature or shape of the subchondral bone is used to estimate curvature or shape of overlying articular cartilage.

11. The method of claim 1, wherein said method is used to assess condition of cartilage in a joint of a human, which method further comprises:

(a) electronically transferring an electronically generated image of a cartilage of the joint from a transferring device to a receiving device located distant from the transferring device;

(b) receiving the transferred image at the distant location;

(c) extracting said cartilage from said transferred image using the method of claim 1;

(d) converting the transferred image to a normal or degeneration pattern of the cartilage; and (e) transmitting said normal or said degeneration pattern to a site for analysis.

12. The method of claim 11, wherein said normal or said degeneration pattern is stored in a database.

13. The method of claim 1, wherein all steps are carried out at an initial time T1 and are carried out again at a later time T2.

14. The method of claim 13, wherein the assessment includes an analysis of the degree of degeneration of the cartilage between T1 and T2.

15. The method of claim 1, wherein said digital image of a cartilage is obtained by a magnetic resonance imaging (MRI) technique.

* * * * *